US008778376B2

(12) United States Patent
Hossainy et al.

(10) Patent No.: US 8,778,376 B2
(45) Date of Patent: *Jul. 15, 2014

(54) COPOLYMER COMPRISING ELASTIN PENTAPEPTIDE BLOCK AND HYDROPHILIC BLOCK, AND MEDICAL DEVICE AND METHOD OF TREATING

(75) Inventors: Syed F. A. Hossainy, Fremont, CA (US); Mikael Trollsas, San Jose, CA (US); Thierry Glauser, Redwood City, CA (US); Yiwen Tang, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1896 days.

This patent is subject to a terminal disclaimer.

(21) Appl. No.: 11/449,896

(22) Filed: Jun. 9, 2006

(65) Prior Publication Data

US 2007/0286885 A1 Dec. 13, 2007

(51) Int. Cl.
*A61F 2/00* (2006.01)
*A61F 2/02* (2006.01)
*A61F 2/04* (2013.01)
*A61F 2/06* (2013.01)
*A61K 9/00* (2006.01)
*A61K 38/43* (2006.01)
*A61K 38/44* (2006.01)
*A61K 38/00* (2006.01)
*A61K 38/08* (2006.01)
*C12N 5/07* (2010.01)
*C12N 11/02* (2006.01)
*C12N 11/08* (2006.01)

(52) U.S. Cl.
USPC ......... 424/423; 424/400; 424/93.1; 424/94.1; 424/94.4; 435/177; 435/180; 514/1.1; 514/21.8

(58) Field of Classification Search
CPC ............... A61F 2/02; A61F 2/04; A61F 2/06; A61K 9/00; A61K 38/43; A61K 38/44; A61K 38/00; A61K 38/08; C12N 5/06; C12N 11/02; C12N 11/08
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,329,383 A | 5/1982 | Joh | |
| 4,343,931 A | 8/1982 | Barrows | |
| 4,529,792 A | 7/1985 | Barrows | |
| 4,611,051 A | 9/1986 | Hayes et al. | |
| 4,656,242 A | 4/1987 | Swan et al. | |
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 4,931,287 A | 6/1990 | Bae et al. | |
| 4,941,870 A | 7/1990 | Okada et al. | |
| 4,977,901 A | 12/1990 | Ofstead | |
| 5,019,096 A | 5/1991 | Fox, Jr. et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,219,980 A | 6/1993 | Swidler | |
| 5,250,516 A * | 10/1993 | Urry ............................... 514/17 |
| 5,258,020 A | 11/1993 | Froix | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,306,786 A | 4/1994 | Moens et al. | |
| 5,328,471 A | 7/1994 | Slepian | |
| 5,330,768 A | 7/1994 | Park et al. | |
| 5,336,256 A * | 8/1994 | Urry ............................ 623/1.44 |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,485,496 A | 1/1996 | Lee et al. | |
| 5,514,380 A * | 5/1996 | Song et al. ..................... 424/426 |
| 5,516,881 A | 5/1996 | Lee et al. | |
| 5,569,463 A | 10/1996 | Helmus et al. | |
| 5,578,073 A | 11/1996 | Haimovich et al. | |

(Continued)

FOREIGN PATENT DOCUMENTS

| | | |
|---|---|---|
| DE | 42 24 401 | 1/1994 |
| EP | 0 301 856 | 2/1989 |

(Continued)

OTHER PUBLICATIONS

International Search Report for PCT/US2007/013687, mailed Jul. 30, 2008, 16 pgs.
Morelli et al., "Structure-activity relationships for some elastin-derived peptide chemoattractants", J. of Peptide Res. vol. 49, No. 6, pp. 492-499 (1997).
Wright et al., "Thermoplastic Elastomer Hydrogels via Self-Assembly of an Elastin-Mimetic Triblock Polypeptide", Adv. Funct. Mater vol. 12, No. 2, pp. 149-154 (2002).
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

(Continued)

*Primary Examiner* — David M Naff
(74) *Attorney, Agent, or Firm* — Squire Patton Boggs (US) LLP

(57) ABSTRACT

A copolymer comprising a block of an elastin pentapeptide and method of making and using the copolymer are provided.

43 Claims, No Drawings

(56) References Cited

U.S. PATENT DOCUMENTS

| | | |
|---|---|---|
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,013,122 A * | 1/2000 | Klitzman et al. ......... 106/31.03 |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,475,779 B2 | 11/2002 | Mathiowitz et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,613,432 B2 | 9/2003 | Zamora et al. |
| 6,616,765 B1 | 9/2003 | Hossainy et al. |
| 6,620,617 B2 | 9/2003 | Mathiowitz et al. |
| 6,623,448 B2 | 9/2003 | Slater |
| 6,625,486 B2 | 9/2003 | Lundkvist et al. |
| 6,641,611 B2 | 11/2003 | Jayaraman |

(56) References Cited

U.S. PATENT DOCUMENTS

| | | | |
|---|---|---|---|
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,689,350 B2 | 2/2004 | Uhrich | |
| 6,695,920 B1 | 2/2004 | Pacetti et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,730,064 B2 | 5/2004 | Ragheb et al. | |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,746,773 B2 | 6/2004 | Llanos et al. | |
| 6,749,626 B1 | 6/2004 | Bhat et al. | |
| 6,753,071 B1 | 6/2004 | Pacetti et al. | |
| 6,758,859 B1 | 7/2004 | Dang et al. | |
| 6,759,054 B2 | 7/2004 | Chen et al. | |
| 6,764,505 B1 | 7/2004 | Hossainy et al. | |
| 6,770,721 B1 * | 8/2004 | Kim | 526/329 |
| 6,776,796 B2 | 8/2004 | Falotico et al. | |
| 6,780,424 B2 | 8/2004 | Claude | |
| 6,790,228 B2 | 9/2004 | Hossainy et al. | |
| 6,824,559 B2 | 11/2004 | Michal | |
| 6,861,088 B2 | 3/2005 | Weber et al. | |
| 6,865,810 B2 | 3/2005 | Stinson | |
| 6,869,443 B2 | 3/2005 | Buscemi et al. | |
| 6,878,160 B2 | 4/2005 | Gilligan et al. | |
| 6,887,270 B2 | 5/2005 | Miller et al. | |
| 6,887,485 B2 | 5/2005 | Fitzhugh et al. | |
| 6,890,546 B2 | 5/2005 | Mollison et al. | |
| 6,890,583 B2 | 5/2005 | Chudzik et al. | |
| 6,899,731 B2 | 5/2005 | Li et al. | |
| 6,926,919 B1 | 8/2005 | Hossainy et al. | |
| 7,008,667 B2 | 3/2006 | Chudzik et al. | |
| 7,173,102 B2 * | 2/2007 | DeGrado et al. | 528/322 |
| 7,601,383 B2 | 10/2009 | Kleiner et al. | |
| 8,029,816 B2 | 10/2011 | Hossainy et al. | |
| 2001/0007083 A1 | 7/2001 | Roorda | |
| 2001/0029351 A1 | 10/2001 | Falotico et al. | |
| 2001/0037145 A1 | 11/2001 | Guruwaiya et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0051730 A1 | 5/2002 | Bodnar et al. | |
| 2002/0077693 A1 | 6/2002 | Barclay et al. | |
| 2002/0082679 A1 | 6/2002 | Sirhan et al. | |
| 2002/0087123 A1 | 7/2002 | Hossainy et al. | |
| 2002/0091433 A1 | 7/2002 | Ding et al. | |
| 2002/0111590 A1 | 8/2002 | Davila et al. | |
| 2002/0165608 A1 | 11/2002 | Llanos et al. | |
| 2002/0176849 A1 | 11/2002 | Slepian | |
| 2002/0183581 A1 | 12/2002 | Yoe et al. | |
| 2002/0188037 A1 | 12/2002 | Chudzik et al. | |
| 2002/0188277 A1 | 12/2002 | Roorda et al. | |
| 2003/0004141 A1 | 1/2003 | Brown | |
| 2003/0028243 A1 | 2/2003 | Bates et al. | |
| 2003/0028244 A1 | 2/2003 | Bates et al. | |
| 2003/0032767 A1 | 2/2003 | Tada et al. | |
| 2003/0036794 A1 | 2/2003 | Ragheb et al. | |
| 2003/0039689 A1 | 2/2003 | Chen et al. | |
| 2003/0040790 A1 | 2/2003 | Furst | |
| 2003/0059520 A1 | 3/2003 | Chen et al. | |
| 2003/0060877 A1 | 3/2003 | Falotico et al. | |
| 2003/0065377 A1 | 4/2003 | Davila et al. | |
| 2003/0072868 A1 | 4/2003 | Harish et al. | |
| 2003/0073961 A1 | 4/2003 | Happ | |
| 2003/0083646 A1 | 5/2003 | Sirhan et al. | |
| 2003/0083739 A1 | 5/2003 | Cafferata | |
| 2003/0097088 A1 | 5/2003 | Pacetti | |
| 2003/0097173 A1 | 5/2003 | Dutta | |
| 2003/0099712 A1 | 5/2003 | Jayaraman | |
| 2003/0105518 A1 | 6/2003 | Dutta | |
| 2003/0113439 A1 | 6/2003 | Pacetti et al. | |
| 2003/0150380 A1 | 8/2003 | Yoe | |
| 2003/0157241 A1 | 8/2003 | Hossainy et al. | |
| 2003/0158517 A1 | 8/2003 | Kokish | |
| 2003/0190406 A1 | 10/2003 | Hossainy et al. | |
| 2003/0207020 A1 | 11/2003 | Villareal | |
| 2003/0211230 A1 | 11/2003 | Pacetti et al. | |
| 2004/0018296 A1 | 1/2004 | Castro et al. | |
| 2004/0029952 A1 | 2/2004 | Chen et al. | |
| 2004/0047978 A1 | 3/2004 | Hossainy et al. | |
| 2004/0047980 A1 | 3/2004 | Pacetti et al. | |
| 2004/0052858 A1 | 3/2004 | Wu et al. | |
| 2004/0052859 A1 | 3/2004 | Wu et al. | |
| 2004/0054104 A1 | 3/2004 | Pacetti | |
| 2004/0060508 A1 | 4/2004 | Pacetti et al. | |
| 2004/0062853 A1 | 4/2004 | Pacetti et al. | |
| 2004/0063805 A1 | 4/2004 | Pacetti et al. | |
| 2004/0071861 A1 | 4/2004 | Mandrusov et al. | |
| 2004/0072922 A1 | 4/2004 | Hossainy et al. | |
| 2004/0073298 A1 | 4/2004 | Hossainy | |
| 2004/0086542 A1 | 5/2004 | Hossainy et al. | |
| 2004/0086550 A1 | 5/2004 | Roorda et al. | |
| 2004/0096504 A1 | 5/2004 | Michal | |
| 2004/0098117 A1 | 5/2004 | Hossainy et al. | |
| 2004/0143322 A1 | 7/2004 | Litvack et al. | |
| 2004/0171545 A1 * | 9/2004 | Chaikof et al. | 514/12 |
| 2005/0033412 A1 | 2/2005 | Wu et al. | |
| 2005/0037052 A1 | 2/2005 | Udipi et al. | |
| 2005/0038134 A1 | 2/2005 | Loomis et al. | |
| 2005/0038497 A1 | 2/2005 | Neuendorf et al. | |
| 2005/0043786 A1 | 2/2005 | Chu et al. | |
| 2005/0049693 A1 | 3/2005 | Walker | |
| 2005/0049694 A1 | 3/2005 | Neary | |
| 2005/0054774 A1 | 3/2005 | Kangas | |
| 2005/0055044 A1 | 3/2005 | Kangas | |
| 2005/0055078 A1 | 3/2005 | Campbell | |
| 2005/0060020 A1 | 3/2005 | Jenson | |
| 2005/0064088 A1 | 3/2005 | Fredrickson | |
| 2005/0065501 A1 | 3/2005 | Wallace | |
| 2005/0065545 A1 | 3/2005 | Wallace | |
| 2005/0065593 A1 | 3/2005 | Chu et al. | |
| 2005/0074406 A1 | 4/2005 | Couvillon, Jr. et al. | |
| 2005/0074545 A1 | 4/2005 | Thomas | |
| 2005/0075714 A1 | 4/2005 | Cheng et al. | |
| 2005/0079274 A1 | 4/2005 | Palasis et al. | |
| 2005/0084515 A1 | 4/2005 | Udipi et al. | |
| 2005/0106210 A1 | 5/2005 | Ding et al. | |
| 2005/0113903 A1 | 5/2005 | Rosenthal et al. | |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |

(56) References Cited

FOREIGN PATENT DOCUMENTS

| | | |
|---|---|---|
| EP | 1 422 242 | 5/2004 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/45941 | 9/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Shigeno, *Prevention of Cerebrovascular Spasm by Bosentan, Novel Endothelin Receptor*, Chemical Abstract 125:212307 (1996).
va Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).
Nagapudi et al., "Viscoelastic and mechanical behavior of recombinant protein elastomers", Biomaterials 26, pp. 4695-4706 (2005).
Reiersen et al., "Short Elastin-like Peptides Exhibit the Same Temperature-induced Structural Transitions as Elastin Polymers: Implications for Protein Engineering", J. Mol. Biol. 283, pp. 255-264 (1998).

* cited by examiner

```
                        SEQUENCE LISTING

<160> NUMBER OF SEQ ID NOS: 6

<210> SEQ ID NO 1
    <211> LENGTH: 5
    <212> TYPE: PRT
    <213> ORGANISM: Artificial Sequence
    <220> FEATURE:
    <223> OTHER INFORMATION: Synthetic peptide

<400> SEQUENCE: 1

Val Gly Val Pro Gly
    1               5

<210> SEQ ID NO 2
    <211> LENGTH: 6
    <212> TYPE: PRT
    <213> ORGANISM: Artificial Sequence
    <220> FEATURE:
    <223> OTHER INFORMATION: Synthetic peptide

<400> SEQUENCE: 2

Ser Ile Lys Val Ala Val
    1               5

<210> SEQ ID NO 3
    <211> LENGTH: 6
    <212> TYPE: PRT
    <213> ORGANISM: Artificial Sequence
    <220> FEATURE:
    <223> OTHER INFORMATION: Synthetic peptide

<400> SEQUENCE: 3

Tyr Ile Gly Ser Arg Gly
    1               5

<210> SEQ ID NO 4
    <211> LENGTH: 5
    <212> TYPE: PRT
    <213> ORGANISM: Artificial Sequence
    <220> FEATURE:
    <223> OTHER INFORMATION: Synthetic peptide
    <220> FEATURE:
    <221> NAME/KEY: misc_feature
    <223> OTHER INFORMATION: Sequence repeats indefinitely

<400> SEQUENCE: 4
```

```
Leu Gly Gly Val Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Sequence repeats indefinitely

<400> SEQUENCE: 5

Val Pro Gly Val Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Val Pro Gly Val Gly
1               5
```

COPOLYMER COMPRISING ELASTIN PENTAPEPTIDE BLOCK AND HYDROPHILIC BLOCK, AND MEDICAL DEVICE AND METHOD OF TREATING

BACKGROUND OF THE INVENTION

1. Field of the Invention

This invention generally relates to elastin-based copolymers for coating an implantable device such as a drug delivery stent or for forming a composition as cell therapy carrier.

2. Description of the Background

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

The existing polymeric coating on a stent can have different types of limitations. For example, some poly(ester amide) based coatings can have poor mechanical properties so as to compromise coating integrity, and coating based on hydrophobic polymers can have problems in controlling release of a hydrophilic drug.

Therefore, there is a need for new carrier materials for controlled delivery of an agent. There is a further need for coating materials for coating a medical device.

The polymer and methods of making the polymer disclosed herein address the above described problems.

SUMMARY OF THE INVENTION

Described in this invention is an elastin-based copolymer. The copolymer can be used to form a coating on a medical device. In some embodiments, the coating can further include a polymer, a biobeneficial material, a bioactive agent, or combinations of these. Some examples of the bioactive agent include, but are not limited to, paclitaxel, docetaxel, estradiol, nitric oxide donors, super oxide dismutases, super oxide dismutases mimics, 4-amino-2,2,6,6-tetramethylpiperidine-1-oxyl(4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, bioactive RGD, CD-34 antibody, abciximab (REOPRO), progenitor cell capturing antibody, prohealing drugs, prodrugs thereof, co-drugs thereof, or a combination thereof.

A medical device having a coating described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, and combinations thereof.

DETAILED DESCRIPTION OF THE INVENTION

Described in this invention is an elastin-based copolymer. The copolymer can be used to form a coating on a medical device. In some embodiments, the coating can further include a polymer, a biobeneficial material, a bioactive agent, or combinations of these. Some examples of the bioactive agent include, but are not limited to, paclitaxel, docetaxel, estradiol, nitric oxide donors, super oxide dismutases, super oxide dismutases mimics, 4-amino-2,2,6,6-tetramethylpiperidine-1-oxyl(4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, bioactive RGD, CD-34 antibody, abciximab (REOPRO), progenitor cell capturing antibody, prohealing drugs, prodrugs thereof, co-drugs thereof, or a combination thereof.

A medical device having a coating described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, and combinations thereof.

Elastin-Based Polymer

Elastin is a protein that is found in the walls of arteries, in lungs, intestines and skin in the body of an animal. Elastin imparts elasticity to the body. Working in partnership with collagen, elastin allows the body organs to stretch and relax. Thus, while collagen provides rigidity, elastin allows the blood vessels and heart tissues, for example, to stretch and then revert to their original positions.

Elastin is found to contain short peptides. The most frequent pentapeptide sequence is valyl-glycyl-valyl-prolyl-glycine (VGVPG) (SEQ ID NO:1). VGVPG is found to exhibit elastin-like properties (see, e.g., Reiersen, H., et al., J. Mol. Biol. 283:255-264 (1998)).

In some embodiments, the elastin-based polymer described herein can be an ABA or BAB type polymer, where A represents a unit that includes the pentapeptide sequence VGVPG (SEQ ID NO: 1) and B represents a unit which can be a peptide sequence or a unit derived from a monomer. The copolymer can be a block or random copolymer.

In some embodiments, the elastin-based copolymer is an ABA triblock copolymer, where A is a block comprising the VGVPG (SEQ ID NO: 1) sequence and B is a block derived from a peptide or monomer(s). In some embodiments, B can be a hydrophilic variant of the VGVPG (SEQ ID NO: 1) peptide. The term "variant" refers to any form of VGVPG (SEQ ID NO: 1) modification. For example, an amino acid in the peptide can be replaced with another amino acid. In some embodiments, the sequence of VGVPG (SEQ ID NO: 1) can be varied so as to form a variant of the VGVPG (SEQ ID NO: 1) peptide. In some embodiments, the VGVPG (SEQ ID NO: 1) peptide can be modified to include lysine (lysine block). This lysine block can be used as the middle block to form the ABA triblock copolymer with the VGVPG (SEQ ID NO: 1) pentapeptide. In these embodiments, the lysine block can be modified to conjugate a molecule or polymer such as phosphoryl choline (PC), poly(ethylene glycol) (PEG), or a bioactive moiety such as nitric oxide generating catalyst or TEMPO as pendant groups. These pendant groups can impart different physical, chemical, or biological properties to the elastin-based polymer.

As one of the properties for the natural elastin materials are usually non-degradable or very slow degradation, degradable linkages can be formed between the peptide blocks so that the newly formed elastin-based materials could be degradable. Any biodegradable polymers described below can be used as the linkage. Some examples of these degradable linkages are poly(lactic acid) (PLA), poly(glycolic acid) (PLGA), polycaprolactone (PCL), poly(3-hydroxybutyric acid (PHB), poly (4-hydroxybutyrate (P4HB), or combinations of these.

In some embodiments, the elastin-based copolymer is an ABA triblock copolymer where A is a block comprising the VGVPG (SEQ ID NO: 1) peptide and B is a hydrophilic synthetic polymer. Such a synthetic polymer can be, for example, a hydrophilic polymer such as PEG, PVP (poly vinylpyrrolidinone), polyacrylamide, poly(PEG acrylate), poly (HEMA), poly(acrylic acid) or combinations of these polymers.

In some embodiments, the elastin-based copolymer is an ABA triblock copolymer where A is a block comprising the VGVPG (SEQ ID NO: 1) peptide and B is a hydrophilic natural polymer such as protein or peptide. In some embodiments, such a hydrophilic natural polymer can be, for example, collagen or collagen derivative, hyaluronic acid, alginate or combinations of these.

In some embodiments, the elastin-based polymer can include a peptide sequence that promotes proliferation and/or migration of endothelial cells (ECs). Such peptide sequence can be, for example, RGD, cRGD, or EC specific sequences such as SIKVAV (SEQ ID NO: 2), CNP, YIGSRG (SEQ ID NO: 3), mimetics of these sequences, or combinations of these.

Composition of Elastin-Based Polymer

In some embodiments, the elastin-based polymer can be used in a composition for cell therapy carrier. For example, the composition can include the elastin-based polymer, cells such as stem cells and optionally other materials and agents. The composition can be delivered to a dysfunctional part of the body (e.g., an organ such as heart or blood vessel) while the cells are still viable. In some embodiments, the composition can include a pharmaceutically acceptable carrier.

Delivery of the composition can be achieved by any established modes of delivery. Preferably, the delivery can be injection or delivery through catheter. In some embodiments, the composition can also be delivered using surgical method such as creating a depot within the muscle and releasing the pharmaceutical agent(s) out of the depot.

Other Biocompatible Polymers

The elastin-based copolymer described herein can be used with other biocompatible polymers. The biocompatible polymer can be biodegradable (either bioerodable or bioabsorbable or both) or nondegradable and can be hydrophilic or hydrophobic. Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly (3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly (methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(etheresters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), molecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof. Some examples of elastin protein mimetics include $(LGGVG)_n$ (SEQ ID NO: 4), $(VPGVG)_n$ (SEQ ID NO: 5), Val-Pro-Gly-Val-Gly (SEQ ID NO: 6), or synthetic biomimetic poly(L-glytanmate)-b-poly (2-acryloyloxyethyllactoside)-b-poly(l-glutamate) triblock copolymer.

In some embodiments, the polymer can be poly(ethylene-co-vinyl alcohol), poly(methoxyethyl methacrylate), poly (dihydroxylpropyl methacrylate), polymethacrylamide, aliphatic polyurethane, aromatic polyurethane, nitrocellulose, poly(ester amide benzyl), co-poly-{[N,N'-sebacoyl-bis-(L- leucine)-1,6-hexylene diester]$_{0.75}$-[N,N'-sebacoyl-L-lysine benzyl ester]$_{0.25}$} (PEA-Bz), co-poly-{[N,N'-sebacoyl-bis-(L-leucine)-1,6-hexylene diester]$_{0.75}$-[N,N'-sebacoyl-L-lysine-4-amino-TEMPO amide]$_{0.25}$} (PEA-TEMPO), aliphatic polyester, aromatic polyester, fluorinated polymers such as poly(vinylidene fluoride-co-hexafluoropropylene), poly(vinylidene fluoride) (PVDF), and Teflon™ (polytetrafluoroethylene), a biopolymer such as elastin mimetic protein polymer, star or hyper-branched SIBS (styrene-block-isobutylene-block-styrene), or combinations thereof. In some embodiments, where the polymer is a copolymer, it can be a block copolymer that can be, e.g., di-, tri-, tetra-, or oligo-block copolymers or a random copolymer. In some embodiments, the polymer can also be branched polymers such as star polymers.

In some embodiments, a coating having the features described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Biobeneficial Material

The elastin-based copolymer can optionally used with a biobeneficial material. The biobeneficial material can be a polymeric material or non-polymeric material. The biobeneficial material is preferably non-toxic, non-antigenic and non-immunogenic. A biobeneficial material is one which enhances the biocompatibility of the particles or device by being non-fouling, hemocompatible, actively non-thrombogenic, or antiinflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol)acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), molecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof. In some embodiments, a coating described herein can exclude any one of the aforementioned polymers. The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly(ethylene glycol) (PEG) or polyalkylene oxide.

Bioactive Agents

The elastin-based copolymer can form a coating on a medical device. The coating can include one or more bioactive agent(s), which can be therapeutic, prophylactic, or diagnostic agent(s). These agents can have anti-proliferative or anti-inflammatory properties or can have other properties such as antineoplastic, antiplatelet, anti-coagulant, anti-fibrin, anti-thrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration or proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, anti-fibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, mometasone, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which can be appropriate include alpha-interferon, pimecrolimus, imatinib mesylate, midostaurin, bioactive RGD, SIKVAV (SEQ ID NO: 2) peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than non-therapeutic levels. The dosage or concentration of the bioactive agent can depend upon factors such as the particular circumstances of the patient, the nature of the trauma, the nature of the therapy desired, the time over which the administered ingredient resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Coating of Elastin-Based Polymer

The elastin-based polymer can be coated on a medical device such as a stent according to an established coating process such as dipping, spray or other processes.

In some embodiments, the coating can be formed by dipping in an aqueous solution of the elastin-based polymer. For example, in some embodiments, a solution of an elastin-based polymer described here can be provided. A medical device such as a stent can be dipped in (rinsed) the solution at a temperature below ambient temperature (e.g., 4° C.). The rinsed medical device can be subject to heat treatment at a temperature in the range of about 15° C.-30° C. higher than the lower critical solution temperature (LCST) of the elastin-based polymer to generate a coating with biomimcry effect.

A solution of the elastin-based polymer can have a concentration of the polymer ranging from about 1 wt % to about 50 wt %. Preferably, the solution has a concentration of the elastin-based polymer in the range between about 5 wt % and about 30%, for example, about 10 wt %, about 15 wt %, about 20 wt % or about 25 wt %. The solution can include a solvent such as water or a biocompatible organic solvent such as dimethylformamide (DMF), dimethyl suloxide (DMSO), dimethyl acetamide (DMAC), methyl ethyl ketone (MEK), ethylene glycol or combinations of these.

In some embodiments, the solvent can be triflouroethanol (TFE). TFE has a boiling temperature of about 80° C., making the solvent a good solvent for use in coating a medical device. The concentration can be varied and determined according to the molecular weight of the elastin-based polymer for forming the coating. For example, with a elastin-based polymer with a weight average molecular weight about 160K Daltons, a solution of the polymer of about 2 wt % in TFE can be used to form a coating on a medical device using spray coating method at room temperature.

In some embodiments, the solution can be an acidic solution having a pH lower than 7. Where an acidic solution of the elastin-based polymer is used to form the coating on a medical device, medical device rinsed or sprayed with the acidic solution shall be rinsed (or sprayed) with a solution of basic pH (>7) buffered solution. Upon pH increase, the elastin-based polymer will come out of the solution and result in a coating on the medical device. The basic buffered solution can be any basic buffer solution in the art.

The mechanical property of the film cast from elastin-based polymer depends on the solution used in the cast. For example, for elongation of the film, generally a pH>7 coating system will lead to a higher elongation than a neutral or acidic water coating system, and a neutral or acidic water coating system will lead to a higher elongation than a TFE coating system.

Examples of Medical Device

As used herein, a medical device can be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, electrodes, pacemaker electrodes, catheters, sensors, endocardial leads (e.g., FINELINE and ENDOTAK, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers or bioabsorbable metals such as magnesium could also be used with the embodiments of the present invention. In some embodiments, the device is a bioabsorbable stent.

Method of Use

In accordance with embodiments of the invention, a medical device having a coating that includes the elastin-based polymer described herein can be used for treating, preventing or ameliorating a medical condition. Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents can be placed in a wide array of blood vessels, both arteries and veins. In some embodiments, the device described herein can be in dialysis, as grafts, or fistulae.

Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features can then be expanded at the desired area of treatment. A post-insertion angiogram can also be utilized to confirm appropriate positioning.

While particular embodiments of the present invention have been shown, and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A block copolymer comprising an elastin pentapeptide block (A) and a hydrophilic block (B),
   wherein the elastin pentapeptide is VGVPG (SEQ ID NO:1),
   wherein the A and B blocks are linked by a biodegradable polymer linkage;
   wherein block B comprises a synthetic polymer selected from polyethylene glycol (PEG), PVP (poly vinylpyrrolidinone), polyacrylamide, poly(PEG acrylate), poly (HEMA), poly(acrylic acid) or combinations of these; and
   wherein the synthetic polymer comprises phosphoryl choline (PC) pendant groups.

2. The block copolymer of claim 1, which is an ABA triblock copolymer.

3. The block copolymer of claim 1, wherein the hydrophilic block further comprises lysine.

4. The block copolymer of claim 2, wherein the hydrophilic block further comprises lysine.

5. The block copolymer of claim 2, wherein the synthetic polymer further comprises poly(ethylene glycol) (PEG) pendant groups.

6. The block copolymer of claim 2, wherein the hydrophilic block further comprises a natural polymer.

7. The block copolymer of claim 1, wherein the synthetic polymer further comprises poly(ethylene glycol) (PEG) pendant groups,
   wherein the PC or PEG is conjugated to the block copolymer via lysine in the hydrophilic block.

8. The block copolymer of claim 1, wherein the synthetic polymer is selected from PEG, PVP (poly vinylpyrrolidinone), polyacrylamide, poly(PEG acrylate), poly (HEMA), or poly(acrylic acid).

9. The block copolymer of claim 6, wherein the natural polymer is selected from collagen, hyaluronic acid, alginate or combinations of these.

10. The block copolymer of claim 1, further comprising a sequence selected from RGD, cRGD, SIKVAV, CNP, YIGSRG, mimetics of these, or combinations of these.

11. The block copolymer of claim 2, further comprising a sequence selected from RGD, cRGD, SIKVAV, CNP, YIGSRG, mimetics of these, or combinations of these.

12. The block copolymer of claim 11, further comprising a sequence selected from RGD, cRGD, SIKVAV (SEQ ID NO: 2), CNP, YIGSRG, (SEQ ID NO: 3), mimetics of these, or combinations of these.

13. The block copolymer of claim 1, wherein the biodegradable linkage is selected from poly(lactic acid) (PLA), poly(glycolic acid) (PLGA), polycaprolactone (PCL), poly (3-hydroxybutyric acid) (PHB), poly(4-hydroxybutyrate (P4HB), or combinations of these.

14. A composition comprising the block copolymer of claim 1, and a cell.

15. A composition comprising the block copolymer of claim 2, and a cell.

16. The composition of claim 14, wherein the cell is stem cell.

17. The composition of claim 14, further comprising a pharmaceutically acceptable carrier.

18. The composition of claim 15, wherein the cell is a stem cell.

19. The composition of claim 15, further comprising a pharmaceutically acceptable carrier.

20. A medical device comprising a coating, the coating comprising the block copolymer of claim 1.

21. A medical device comprising a coating, the coating comprising the block copolymer of claim 2.

22. A medical device comprising a coating, the coating comprising the block copolymer of claim 3.

23. A medical device comprising a coating, the coating comprising the block copolymer of claim 4.

24. A medical device comprising a coating, the coating comprising the block copolymer of claim 5.

25. A medical device comprising a coating, the coating comprising the block copolymer of claim 6.

26. A medical device comprising a coating, the coating comprising the block copolymer of claim 7.

27. A medical device comprising a coating, the coating comprising the block copolymer of claim 8.

28. A medical device comprising a coating, the coating comprising the block copolymer of claim 9.

29. A medical device comprising a coating, the coating comprising the block copolymer of claim 10.

30. A medical device comprising a coating, the coating comprising the block copolymer of claim 11.

31. A medical device comprising a coating, the coating comprising the block copolymer of claim 12.

32. A medical device comprising a coating, the coating comprising the block copolymer of claim 13.

33. The medical device of claim 20, wherein the coating further comprises a bioactive agent.

34. The medical device of claim 33, wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these.

35. The medical device of claim 34, which is a stent.

36. The medical device of claim 34, which is a bioabsorbable stent.

37. A method of treating, preventing or ameliorating a medical condition, comprising providing a composition according to claim 14, and delivering the composition to a human having the medical condition.

38. A method of treating, preventing or ameliorating a medical condition, comprising providing a composition according to claim 15, and delivering the composition to a human having the medical condition.

39. The method of claim 37, wherein the medical condition pertains to an organ of the human.

40. The method of claim 39, wherein the organ is heart.

41. The method of claim 39, wherein the organ is blood vessel.

42. A method of treating, preventing or ameliorating a disorder in a patient comprising implanting in the patient the medical device of claim 33, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

43. A method of treating, preventing or ameliorating a disorder in a patient comprising implanting in the patient the medical device of claim 34, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

* * * * *

UNITED STATES PATENT AND TRADEMARK OFFICE
CERTIFICATE OF CORRECTION

| | | |
|---|---|---|
| PATENT NO. | : 8,778,376 B2 | Page 1 of 1 |
| APPLICATION NO. | : 11/449896 | |
| DATED | : July 15, 2014 | |
| INVENTOR(S) | : Hossainy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2030 days.

Signed and Sealed this
Seventeenth Day of November, 2015

Michelle K. Lee
*Director of the United States Patent and Trademark Office*